United States Patent [19]

Brunner

[11] 3,969,465

[45] July 13, 1976

[54] PROCESS FOR RECOVERY OF CARBOXYLIC ACIDS FROM THE WASTE SALT SOLUTIONS OF CYCLOHEXANONE MANUFACTURE

[76] Inventor: Josef Klemens Brunner, Scheuchzerstrasse 47, Zurich, Switzerland

[22] Filed: Nov. 18, 1974

[21] Appl. No.: 524,492

[30] Foreign Application Priority Data

Nov. 19, 1973 Australia.............................. 9682/73

[52] U.S. Cl. ......................... 260/527 R; 260/484 R; 260/485 R; 260/488 F; 260/535 R; 260/537 P; 260/540; 260/541; 260/542
[51] Int. Cl.² .................... C07C 51/44; C07C 51/48
[58] Field of Search......... 260/527 R, 535 R, 537 P, 260/540, 541, 542

[56] References Cited
UNITED STATES PATENTS

| | | | |
|---|---|---|---|
| 2,714,118 | 7/1955 | Copenhaver et al. ............ | 260/527 R |
| 2,859,154 | 11/1958 | Othmer ............................ | 260/527 R |

*Primary Examiner*—Vivian Garner
*Attorney, Agent, or Firm*—William R. Woodward

[57] ABSTRACT

Waste salt solution from cyclohexanone manufacture is acidulated in a neutralizer, after which the organic phase is separated and subjected to a counter-current extraction with a saturated aqueous solution of mostly monocarboxylic acids separated from a later stage of the process. The watery extract carries off sodium sulphate that would otherwise interfere with further refining and this extract is then returned to the neutralizing vessel where the waste salt solutions are being acidulated, thereby reducing the need for externally supplied water to keep sodium sulphate from precipitating in the neutralizer and also enabling the dissolved monocarboxylic acids to be recovered. The organic phase leaving the counter-current extractor then goes to a flash evaporator in a condition now free of sodium sulphate, so that the evaporator may continuously remove water and monocarboxylic acids, which are then condensed and separated, with the water phase going back to the extractor as previously mentioned. The outputs are a mixture of monocarboxylic acids from the last separator and a mixture of dicarboxylic acids and hydroxy acids from the liquid coming out of the evaporator.

4 Claims, 1 Drawing Figure

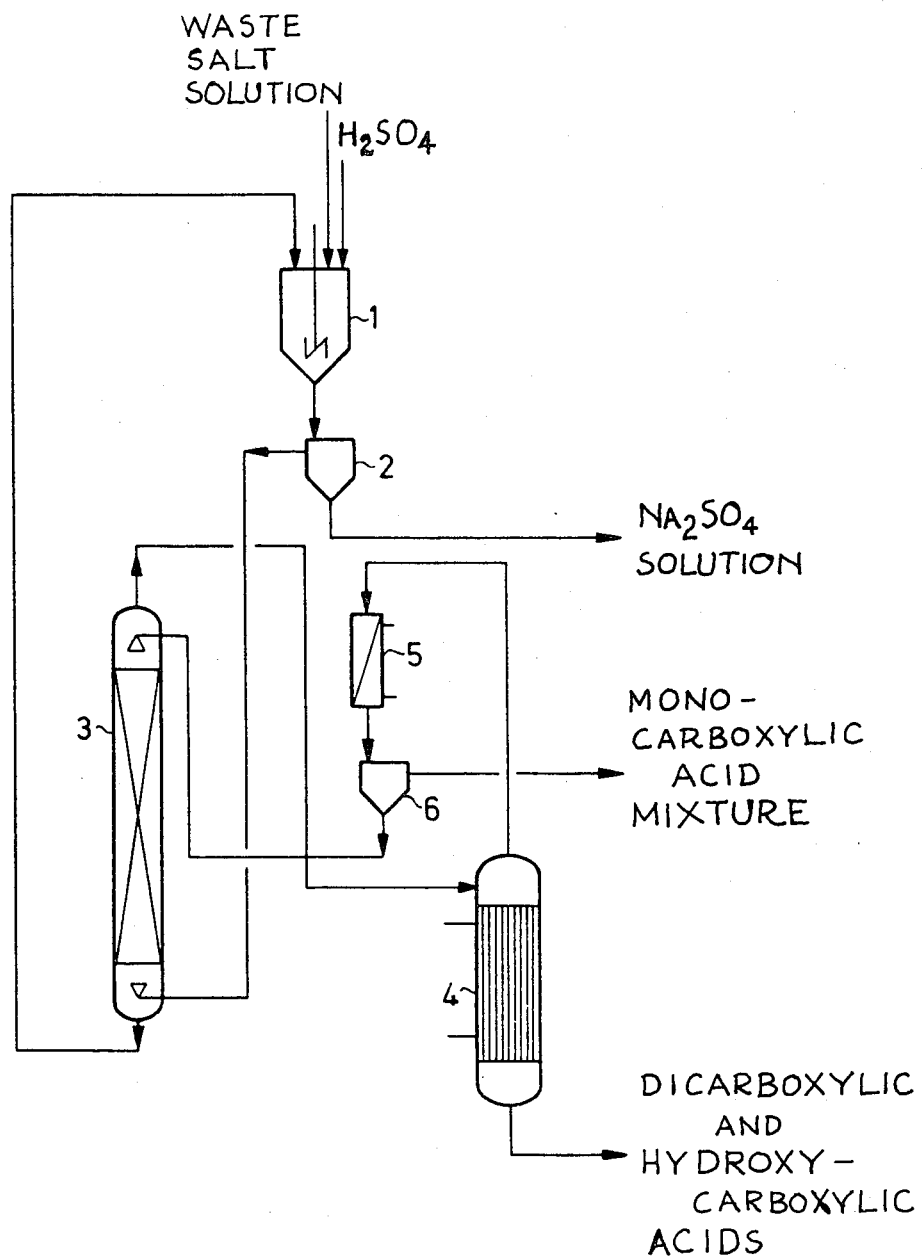

PROCESS FOR RECOVERY OF CARBOXYLIC ACIDS FROM THE WASTE SALT SOLUTIONS OF CYCLOHEXANONE MANUFACTURE

This invention relates to an improved method of obtaining useful organic acids from the waste solutions resulting from cyclohexanone manufacture. The acids as obtained from the present process are particularly useful to produce esters that are valuable as solvents, by means of a subsequent esterification step.

In the manufacture of cyclohexanone by catalytic oxidation of cyclohexane with oxygen a reaction mixture is produced that contains, in addition to the desired products, rather larger quantities of various saturated monocarboxylic and dicarboxylic acids. Before further treatment of the reaction mixture, the acids are treated with water and/or alkali solutions so that they are obtained in the form of a concentrated aqueous solution of their salts. Such solutions constitute an undesired and inconvenient by-product of the production of cyclohexane. They contain, more or less, the following quantities of carboxylic acids in the form of their sodium salts:

| ACID | % BY WEIGHT |
| --- | --- |
| Formic, acetic & propionic | 0.75 |
| Butyric | 0.50 |
| Valeric | 9.25 |
| Caproic | 6.75 |
| Hydroxycaproic | 4.40 |
| Succinic & glutaric | 0.25 |
| Adipic | 2.0 |

Along with these there are also contained small quantities of other organic materials, particularly also resins.

There has been no lack of experiments to do something with these solutions, because considerable costs are involved in their destruction or other disposition. Japanese patent No. 68 17 163 describes a process in which these solutions are first acidulated with mineral acids to a pH value of 0.7 to 3, after which the two resulting phases are separated and the organic phase is extracted with a halogenated hydrocarbon. The extract is freed of the solvent by evaporation and the remainder is then separated into the individual monocarboxylic acids by fractionation. This process cannot operate economically, since out of 3,000 kg of waste salt solution, with addition of 400 kg of sulphuric acid, only 130 kg of monocarboxylic acids can be obtained.

A better suggestion is made in Polish patent No. 54,750; where the waste salt solution is described as being neutralized to a pH value of 5 with sulphuric acid and then cooled to 18°C. Two phases are produced, of which the upper organic phase is separated and distilled with steam. This distillate also divides into two phases, of which the upper organic phase is then fractioned. Valeric and caproic acids are obtained as products. Here, also, there is the disadvantage that with a relatively high expense only two materials are obtained as products and the others not only are lost in the materials contained in the waste salt solution, but cause additional costs for the necessary destruction of the waste material.

A substantial advance was provided by the treatment described in the patent application of the present inventor jointly with Hellmuth Schindlbauer and Walter Eichberger, Ser. No. 372,021, filed June 21, 1973, now U.S. Pat. No. 3,859,335.

In that treatment, the waste salt solution is first acidulated with a strong acid, thus setting free the carboxylic acids. Two phases are produced, a concentrated sodium sulphate solution and a water-containing mixture of carboxylic acids that is then given further treatment. The carboxylic acids still in solution are removed from the sodium sulphate solution by an extraction and thus recovered. The carboxylic acid mixture is separated by distillation into a distillate containing the water and the volatile monocarboxylic acids and a residue remaining as a mother liquor containing the dicarboxylic acids and hydroxycarboxylic acids. The monocarboxylic acids are esterified with isobutanol and the dicarboxylic and hydroxycarboxylic acids with methanol. The esters of the monocarboxylic acids, as well as those of the dicarboxylic and hydroxycarboxylic acids, can be used as solvents.

The above-described process constitutes a genuine advance, because in this way it is possible to convert the waste salt solution practically fully into salable products. As the result of the larger quantity of salable products, it is possible not only to obtain greater monetary proceeds, but also to save the costs of an otherwise necessary waste disposal installation for the other products.

In carrying out the process of the aforesaid application Ser. No. 372,021, however, difficulties still remain: the separation of the organic from the inorganic phase after neutralization is not complete, i.e. in the organic phase there is found, along with the carboxylic acids, not only about 25% water content, but also sodium sulphate in an amount from 0.3 to 3%. In the subsequent distillation the water is of course removed, but the sodium sulphate precipitates out and forms an encrustation on the heat exchanger surfaces. When thin layer evaporators are used, there is a great amount of wear, moreover, on the wiper blades. The operational reliability of the evaporator is therefore not sufficient for a commercial scale operation and it is necessary to wash the heat exchange surface of the evaporator with water across a small spacing, that produces a considerable loss not only of operating time, but also of carboxylic acid recovery. Furthermore, the recovered wash water must be treated, because on account of its carboxylic acid content, it cannot normally be discharged as waste water. As a result of these difficulties, the economic viability of the process of the aforesaid application is limited.

Attempts to remove the dissolved sodium sulphate by subjecting the organic phase containing the carboxylic acids to extraction before the distillation have been unsuccessful prior to the present invention. On account of the good water solubility of the lower monocarboxylic acids, hydroxycarboxylic acids and dicarboxylic acids, a considerable proportion of these materials were extracted along with the sodium sulphate. To get these acids back out of the extraction solution, for example by extraction with another solvent, is very difficult, because these acids are very hydrophilic, i.e. the partition coefficients for organic solvents that are not miscible with water are very unfavorable.

SUBJECT MATTER OF THE PRESENT INVENTION

Surprisingly, it has been found possible to avoid these difficulties and to improve the reliability and safety of the necessary apparatus without loss of carboxylic acids by providing a counter-current extraction prior to the distillation of the organic phase separated from the acidulated salt solution, in which the organic phase is subjected to an extraction with the aqueous solution of monocarboxylic acids which is obtained in the subsequent distillation of the extracted organic phase. In that distillation the vapors are condensed, the organic phase that forms is separated and the aqueous solution is used for the aforesaid extraction and then fed back into the neutralization stage of the waste salt solution.

The solution used for the extraction of the sodium sulphate contained in the organic acid mixture is in fact already saturated with the lower monocarboxylic acids, which are particularly well soluble in water, as the result of which saturation the loss of these acids from the carboxylic acid mixture is essentially prevented. Even after the extraction the aqueous extraction solution contains rather little sodium sulphate along with the dissolved carboxylic acid, namely 2 to 8% by weight of $Na_2SO_4$, so that it is still far from saturation.

The sodium sulphate content influences the extractability of the carboxylic acids very strongly, an effect known as the "salting out effect". The recovery of carboxylic acids from a dilute sodium sulphate solution is therefore substantially more difficult than from a solution saturated with sodium sulphate. The recovery of the carboxylic acids from the solution mentioned just above, which contains only little sodium sulphate, is therefore complicated and expensive. According to the invention, this solution is not further treated for recovery purposes, but instead is mixed in to contribute to the acidulation of the waste salt solution. The waste salt solutions are mostly so concentrated that when conversion with concentrated sulphuric acid takes place, a supersaturation of sodium sulphate occurs, which means that, before the separation of the two phases that form, water is usually added in order to prevent the precipitation of sodium sulphate. This water can now be replaced, in the process of the present invention, by the aforementioned sodium sulphate containing extract, so as to make unneccessary its further treatment as well as to reduce substantially the amount of waste water resulting from the process taken as a whole. Since the solubility of the sodium sulphate in water is strongly dependent upon temperature and has a maximum at +32°C, and since the neutralization liberates a considerable amount of heat, it is desirable from a practical standpoint to provide the appropriate amount of cooling to hold the temperature at or close to this value.

The process of the present invention is illustrated by a flow diagram given in the single FIGURE of the accompanying drawing.

The waste salt solution, concentrated sulphuric acid (96–98& $H_2SO_4$) and the sodium sulphate and water extract saturated with dissolved carboxylic acids are continuously fed into the neutralization vessel 1 in such relative quantities that sodium ions and sulphate ions are contained in stoichiometric proportions and so that the aqueous phase which is separated in the phase separator 2 is practically saturated with sodium sulphate. The temperature within the neutralizing vessel 1 is held at about 32°C by either external or internal cooling means (not shown).

The organic phase, which is drawn off from the upper part of the phase separator 2 and consists of the mixture of carboxylic acids, is then led into the extractor 3 where it is subjected to a counter-current extraction with the watery part of the condensate from the fractionation stage that follows the extraction. The aqueous extract, as already mentioned above, is led back into the neutralization vessel 1. The carboxylic acid mixture which has been subjected to the extraction and is drawn off at the top of the extraction vessel 3 is then heated under vacuum in a thin layer evaporator 4. The remaining liquid that runs out of the evaporator consists of a mixture containing predominantly dicarboxylic acids and hydroxy acids. The vapors that come off through the flash evaporation are condensed in the condenser 5 and drained into a phase separator 6 where the two phases that are produced are separated. The organic phase consists of a mixture of monocarboxylic acids that still contains a little water and the aqueous phase is in the form of a saturated solution of these acids in water. As already mentioned, it is used in the extractor 3 for removal of the sodium sulphate. The organic products of the process illustrated in the drawing are two mixtures of carboxylic acids, first a mixture of monocarboxylic acids from the phase separator 6 and, second, a mixture of dicarboxylic acids and hydroxycarboxylic acids drawn off the bottom of the evaporator 4. These mixtures may each be subjected to an esterification stage to produce useful esters and the esters may be used in mixed form in the formulating of solvents or they may be further refined by distillation or transesterification and distillation or extraction if desired. Examples of the utility of esters of these kinds are given in co-pending applications of the present inventor, Ser. No. 516,657 and 516,659, filed Oct. 21, 1974.

A typical waste salt solution from the manufacture of cyclohexanone used in the process of this invention has a pH of 8.5–11. In the acidulation step in which concentrated sulphuric acid and the saturated organic acid solution from the extractor are added, the pH is reduced to 1–2.5, this being the pH of the mixture which goes to the separator 2 shown in the drawing.

The evaporator 4 in a typical operation of the process of this invention is operated at a temperature of about 85°C, generally in the range from 80° to 100°C under vacuum, which is to say at a pressure typically 0.02 atm. and generally within the range from 0.001 to 0.07 atm. The means for applying the vacuum, like the means for applying heat to the evaporator 4 and cooling to the neutralizer 1 and to the condenser 5 are omitted in the drawing to simplify the illustration. The temperature of the condenser 5 is such that the condensate comes out at a temperature of 30°C. By the time the aqueous phase comes out of the separator 6 and is put into the top of the extractor 3 its temperature is typically about 25°C.

Although the waste salt solution from cyclohexanone manufacture typically is a solution of sodium salts, it is conceivable that other metal salts might be present for some reason and the process of the invention as above described would be equally applicable so long as the metal forms a soluble sulphate, although of course the above recommended temperature for the neutralizer pertains particularly to the treatment of sodium salts.

I claim:

1. In a process for obtaining usefully esterifiable organic acids from the waste solution of salts of monocarboxylic acids having 1 to 6 carbon atoms, dicarboxylic acids and hydroxy carboxylic acids produced in the manufacture of cyclohexanone by the catalytic oxidation of cyclohexane, in which said waste salt solution is acidulated with sulfuric acid to produce an aqueous phase which is a concentrated sulfate salt solution and an organic phase which is a water-containing mixture of free carboxylic acids, said phases are separated and the organic phase is separated by distillation into a distillate containing water and monocarboxylic acids and a residue containing dicarboxylic and hydroxy acids, the improvement which consists in that:

in the acidulation step there is added to the said waste salt solution concentrated sulfuric acid and also an aqueous solution of monocarboxylic acids derived from a separated aqueous phase from the distillate produced in the distillation step, the acidulation step being performed so as to lower the pH of the salt solution to a value in the range between 1 and 2.5;

the water-containing mixture of carboxylic acids separated as an organic phase from the concentrated sulfate solution is subjected, prior to distillation, to a counter-current extraction with a saturated aqueous solution of monocarboxylic acids obtained as a distillate and retrocycled from the distillation step, the aqueous extract obtained by said counter-current extraction being then recycled to the acidulation step; and the distillation step is performed on the water-containing carboxylic acid mixture obtained after said counter-current extraction by subjecting it to heat under vacuum in a thin film evaporator to vaporize out water and monocarboxylic acids and to produce a remainder liquid consisting mainly of dicarboxylic acids and one or more hydroxy acids, condensing the distillate vapors to form a condensate, and separating the condensate into an aqueous saturated solution of monocarboxylic acids for retrocycling as aforesaid and an organic phase comprising the monocarboxylic acid product of the process.

2. Process as defined in claim 1, in which the salts of said waste salt solution consist essentially of sodium salts and in which the acidulation step is performed in a vessel provided with cooling means operated to maintain the temperature of the contents at about 32°C.

3. Process as defined in claim 2, in which the acidulation step is performed in a manner maintaining sodium ions and sulphate ions in solution in at least approximately stoichiometric proportions.

4. Process as defined in claim 1, in which said evaporator is heated to a temperature in the range from 80° to 100°C and a vacuum of 0.001 to 0.07 atm. is applied thereto.

* * * * *